United States Patent [19]

Antoniades et al.

[11] Patent Number: 5,034,375
[45] Date of Patent: Jul. 23, 1991

[54] PROCESS OF WOUND HEALING USING PDGF AND EGF

[75] Inventors: Harry N. Antoniades, Newton; Samuel E. Lynch, Jamaica Plain, both of Mass.

[73] Assignees: Institute of Molecular Biology, Inc., Boston; President and Fellows of Harvard College, Cambridge, both of Mass.

[21] Appl. No.: 231,145

[22] Filed: Aug. 10, 1988

[51] Int. Cl.$^5$ .................... A61K 37/02; A61K 37/36
[52] U.S. Cl. ........................................ 514/12; 514/8; 514/21
[58] Field of Search .............................. 514/21, 12, 8

[56] References Cited

U.S. PATENT DOCUMENTS

| | | | |
|---|---|---|---|
| 4,085,204 | 4/1978 | Wacker et al. | 424/101 |
| 4,350,687 | 9/1982 | Lipton et al. | 424/177 |
| 4,479,896 | 10/1984 | Antoniades | 530/380 |
| 4,604,234 | 8/1986 | Fujii et al. | 514/2 |
| 4,702,908 | 10/1987 | Thorbecke et al. | 424/88 |
| 4,742,003 | 5/1988 | Derynck et al. | 435/68 |
| 4,745,179 | 5/1988 | Ueda et al. | 530/350 |

FOREIGN PATENT DOCUMENTS 0267015 4/1987 European Pat. Off. .
0312208 4/1989 European Pat. Off. .

OTHER PUBLICATIONS

Betsholtz et al., "Growth Factor-Induced Proliferation of Human Fibroblasts in Serum-Free Culture Depends on Cell Density and Extracellular Calcium Concentration," J. of Cellular Physio., 118: 203-210 (1984).
Canalis, "Effect of Platelet-Derived Growth Factor on DNA and Protein Synthesis in Cultured Rat Calvaria," Metabolism, 30: 970-975 (1981).
Clemmons et al., "Somatomedin-C and Platelet-Derived Growth Factor Stimulate Human Fibroblast Replication," J. of Cellular Physio., 106: 361-367 (1981).
Computer print out of various patent abstracts.
Grotendorst, "Can Collagen Metabolism Be Controlled?", J. of Trauma 24: 549-552 (1984).
Grotendorst et al., "Molecular Mediators of Tissue Repair," in *Soft and Hard Tissue Repair*, Hunt et al. eds., Praeger Scientific, 1984, pp. 20-40.
Grotendorst et al., "Stimulation of Granulation Tissue Formation by Platelet-Derived Growth Factor in Normal and Diabetic Rats," J. Clin. Invest. 76: 2323-2329 (1985).
Hebda, "The Effects of Peptide Growth Factors on Epidermal Outgrowth in an in Vitro Wound Healing Model", J. of Cell Biology, 107: p. 46A (1989).
Heldin et al., "Growth of Normal Human Glial Cells in a Defined Medium Containing Platelet-Derived Growth Factor," Proc. Natl. Acad. Sci. U.S.A., 77: 6611-6615 (1980).
Kabigen Commercial literature, "Human Cell Growth Factors for Cell Growth and Differentiaton".
Lawrence et al., "The Reversal of an Adriamycin Induced Healing Impairment with Chemoattractants and Growth Factors," Ann. Surg., 203: 142-147 (1986).
Leal et al., "Evidence That the V-Sis Gene Product Transforms by Interaction with the Receptor for Platelet-Derived Growth Factor," Science, 230: 327-330 (1985).
Leitzel et al., "Growth Factors and Wound Healing in the Hamster," J. Dermatol. Surg. Oncol., 11: 617-621 (1985).
Lynch et al., "Role of Platelet-Derived Growth Factor in Wound Healing: Synergistic Effects With Other Growth Factors," Proc. Natl. Acad. Sci. U.S.A., 84: 7696-7700 (1987).
Michaeli et al., "The Role of Platelets in Wound Healing: Demonstration of Angiogenic Activity," *Soft and Hard Tissue Repair*, Hunt et al., eds., Praeger Scientific, 1984 pp. 380-394.
Mustoe et al., "Accelerated Healing of Incisional Wounds in Rats Induced by Transforming Growth Factor-B," Science, 237: 1333-1336 (1987).
Roberts et al., "Type B Transforming Growth Factor: A Bifunctional Regulator of Cellular Growth," Proc. Natl. Acad. Sci. U.S.A., 82: 119-123 (1985).
Reddan et al., "Insulin-Like Growth Factors, IGF-1, IGF-2 and Somatomedin C Trigger Cell Proliferation in Mammalian Epithelial Cells Cultured in a Serum-Free Medium," Exp. Cell Res., 142: 293-300 (1982).
Rinderknecht et al., "Primary Structure of Human Insulin-Like Growth Factor II," Proc. Natl. Acad. Sci. U.S.A., 89: 283-286 (1978).
Ross et al., "The Biology of Platelet-Derived Growth Factor," Cell, 46: 155-169 (1986).
Schultz et al., "Epithelial Wound Healing Enhanced by Transform Growth Factor," Chemical Abstracts, 106: 96915h (1987).
Shipley et al., "Reversible Inhibition of Normal Human Prokeratinocyte by Type B Transforming Factor-Growth Inhibitor in Serum-Free Medium," Cancer Research, 46: 2068-2071 (1986).
Sporn et al., "Polypeptide Transforming Growth Factors Isolated from Bovine Sources and Used for Wound Healing in Vivo," Science, 219: 1329-1331 (1983).
Sporn et al., "Repair of Tissue in Animal", U.S. Ser. No. 468,590, date filed 2/22/83.
Stiles et al., "Dual Control of Cell Growth by Somatomedins and Platelet Derived Growth Factor," Proc. Natl. Acad. Sci. U.S.A., 76: 1279-1283 1979.
Tashjian et al., "Platelet-Derived Growth Factor Stimulates Bone Resorption via a Prostaglandin-Mediated Mechanism," Endocrinology, 111: 118-124 (1982).
Van Wyk et al., "Role of Somatomedin in Cellular Proliferation in *The Biology of Normal Human Growth*," edited by M. Ritzen et al., Raven Pres. pp. 223-239 (1981).
Devel et al., (1984) J. Clin. Invest. 74:669.

*Primary Examiner*—Howard E. Schain
*Attorney, Agent, or Firm*—Fish & Richardson

[57] ABSTRACT

Healing an external wound of a mammal by administering to the mammal a composition containing purified EGF and purified PDGF in a weight to weight ratio of at least 5:1.

4 Claims, No Drawings

PROCESS OF WOUND HEALING USING PDGF AND EGF

BACKGROUND OF THE INVENTION

This invention relates to healing wounds.

Growth factors are polypeptide hormones which stimulate a defined population of target cells. Examples of growth factors include platelet-derived growth factor (PDGF), insulin-like growth factor, transforming growth factor beta (TGF-$\beta$), transforming growth factor alpha, epidermal growth factor (EGF), and fibroblast growth factor. PDGF is a cationic, heat-stable protein found in the granules of circulating platelets which is known to stimulate in vitro protein synthesis and collagen production by fibroblasts. It is also known to act as an in vitro mitogen and chemotactic agent for fibroblasts, and smooth muscle cells.

It has been proposed to use PDGF to promote in vivo wound healing. For example, Grotendorst (1984) J. Trauma 24:549-52 describes adding PDGF to Hunt-Schilling wire mesh chambers impregnated with a collagen gel and implanted in the backs of rats; PDGF was found to increase the amount of new collagen synthesized. However, Leitzel et al. (1985) J. Dermatol. Surg. Oncol. 11:617-22 were unable to accelerate normal wound healing in hamsters using PDGF alone or in combination with FGF and EGF.

Michaeli, et al. (1984) In Soft and Hard Tissue Repair (Hunt, T.K. et al., Eds), Praeger Publishers, New York, pp. 380-394, report that application of a partially purified preparation of PDGF obtained from platelet-rich plasma stimulated angiogenesis when implanted in rabbit corneas. Because PDGF is not an angiogenic growth factor the investigators suggested that an unknown factor in their partially purified PDGF preparation was responsible for the angiogenic effect.

Lawrence et al. 203 Ann. Surgery 142, 1986 demonstrate a synergisic wound healing activity when TGF-$\beta$, PDGF and EGF are used together at 100 ng/ml each but not with PDGF in combination with EGF alone. Lynch et al. 84 Proc. Nat. Acad. Sci. USA 7696, 1987 state that a preparation containing equal amounts (5ng/mm$^2$) of EGF and PDGF did not elicit wound healing activity greater than that brought about by EGF or PDGF alone.

SUMMARY OF THE INVENTION

In general, the invention features healing an external wound in a mammal, e.g., a human patient, by applying to the wound an effective amount of a composition that includes a combination of purified EGF and purified PDGF, in a weight to weight ratio of at least 5:1, preferably at least 10:1. Preferably, the EGF is recombinant human EGF, but can also be of another mammalian species, e.g., rat. EGF can be isolated from natural sources or, more preferably, produced by recombinant cells or solid phase peptide synthesis. The composition of the invention aids in healing the wound, at least in part, by promoting the growth of epithelial and connective tissue and the synthesis of total protein and collagen. Wound healing using the composition of the invention is more effective than that achieved in the absence of treatment (i.e., without applying exogenous agents) or by treatment with purified PDGF alone, or purified EGF alone.

In preferred embodiments of the invention, the composition is prepared by combining, in a pharmaceutically acceptable carrier substance, e.g., commercially available inert gels, liquids, or other slow release delivery systems (e g., saline supplemented with albumin or methyl cellulose), purified EGF and PDGF (both of which are commercially available) in a weight-to-weight ratio of between 5:1 and 10:1, or greater than 10:1. The purified PDGF may be obtained from human platelets or by recombinant DNA technology. Thus, by the term "PDGF" we mean both platelet-derived and recombinant materials of mammalian, preferably primate, origin; most preferably, the primate is a human, but can also be a chimpanzee or other primate. Recombinant PDGF can be recombinant heterodimer, made by inserting into cultured prokaryotic or eukaryotic cells DNA sequences encoding both subunits, and then allowing the translated subunits to be processed by the cells to form heterodimer, or DNA encoding just one of the subunits (preferably the beta or "2" chain) can be inserted into cells, which then are cultured to produce homodimeric PDGF (PDGF-1 or PDGF-2 homodimer).

The term "purified" as used herein refers to PDGF or EGF which, prior to mixing with the other, is 95% or greater, by weight, PDGF or EGF, i.e., is substantially free of other proteins, lipids, and carbohydrates with which it is naturally associated.

A purified protein preparation will generally yield a single major band on a polyacrylamide gel for each PDGF or EGF component. Most preferably, the purified PDGF or EGF used in the composition of the invention is pure as judged by amino-terminal amino acid sequence analysis.

The invention also features healing an external wound by applying at least 500 ng/150 mm$^2$ of EGF to the wound, preferably at least 5000 ng/150 mm$^2$, in combination with purified PDGF.

The composition of the invention provides a fast, effective method for healing external wounds of mammals, e.g., bed sores, lacerations, corneal wounds and burns. The composition enhances connective tissue formation compared to natural healing (i.e. no exogenous agents added) or pure PDGF or EGF alone. Unlike pure PDGF alone, the composition promotes a significant increase in both new connective tissue and epithelial tissue. The epithelial layer obtained is thicker than that created by natural healing or by EFG alone, and also contains more epithelial projections connecting it to the new connective tissue; it is thus more firmly bound and protective.

Other features and advantages of the invention will be apparent from the following description of the preferred embodiments thereof, and from the claims.

DESCRIPTION OF THE PREFERRED EMBODIMENTS

We now describe preferred embodiments of the invention.

External wounds, e.g., bed sores, diabetic ulcers and burns, are treated, according to the invention, with PDGF/EGF mixtures prepared by combining pure PDGF and EGF. Recombinant human EGF is commercially available from Amgen (Thousand Oaks, Calif.) and Collaborative Research (Bedford, Mass.). Purified recombinant PDGF and purified PDGF derived from human platelets are commercially available from PDGF, Inc. (Boston, Mass.), Collaborative Research (Waltham, Mass.), and Amgen Corp. Purified PDGF can also be prepared as follows.

Five hundred to 1000 units of washed human platelet pellets are suspended in 1M NaCl (2 ml per platelet unit) and heated at 100° C. for 15 minutes. The supernatant is then separated by centrifugation and the precipitate extracted twice with the 1M NaCl.

The extracts are combined and dialyzed against 0.08M NaCl-0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl-0.01M sodium phosphate buffer (pH 7.4), and eluted with 1M NaCl while 10 ml fractions are collected.

Active fractions are pooled and dialyzed against 0.3M NaCl 0.01M sodium phosphate buffer (pH 7.4), centrifuged, and passed at 4° C. through a 2.5×25 cm column of Blue Sepharose (Pharmacia) equilibrated with 0.3M NaCl-0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl-0.01M sodium phosphate buffer (pH 7.4) and passed through a 1.2×40 cm column of CM-Sephadex C-50 equilibrated with the buffer. PDGF is then eluted with a NaCl gradient (0.08 to 1M).

The active fractions are combined, dialyzed against 1M acetic acid, lyophilized, and dissolved in a small volume of 1M acetic acid. 0.5 ml portions are applied to a 1.2×100 cm column of Biogel P-150 (100 to 200 mesh) equilibrated with 1M acetic acid. The PDGF is then eluted with 1M acetic acid while 2 ml fractions are collected.

Each active fraction containing 100 to 200 mg of protein is lyophilized, dissolved in 100 ml of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF made by recombinant DNA technology can be prepared as follows:

Platelet-derived growth factor (PDGF) derived from human platelets contains two polypeptide sequences (PDGF-1 and PDGF-2 polypeptides; Antoniades, H. N. and Hunkapiller, M. (1983) Science 220:963-965). PDGF-1 is encoded by a gene localized in chromosome 7 (Betsholtz, C. et al., Nature 320:695-699), and PDGF-2 is encoded by the sis oncogene (Doolittle, R. et al. (1983) Science 221:275-277) localized in chromosome 22 (Dalla-Favera, R. (1982) Science 218:686-688). The sis gene encodes the transforming protein of the Simian Sarcoma Virus (SSV) which is closely related to PDGF-2 polypeptide. The human cellular c-sis also encodes the PDGF-2 chain (Rao, C D. et al. (1986) Proc. Natl. Acad. Sci. USA 83:2392-2396). Because the two polypeptide chains of PDGF are coded by two different genes localized in separate chromosomes, the possibility exists that human PDGF consists of a disulfide-linked heterodimer of PDGF-1 and PDGF-2, or a mixture of the two homodimers (homodimer of PDGF-1 and homodimer of PDGF-2), or a mixture of the heterodimer and the two homodimers.

Mammalian cells in culture infected with the Simian Sarcoma Virus, which contains the gene encoding the PDGF-2 chain, were shown to synthesize the PDGF-2 polypeptide and to process it into a disulfide-linked homodimer (Robbins, K. et al. (1983) Nature 305:605-608). In addition, PDGF-2 homodimer reacts with antisera raised against human PDGF. Furthermore, the functional properties of the secreted PDGF-2 homodimer are similar to those of platelet-derived PDGF in that it stimulates DNA synthesis in cultured fibroblasts, it induces phosphorylation at the tyrosine residue of a 185 kd cell membrane protein, and it is capable of competing with human ($^{125}$I)-PDGF for binding to specific cell surface PDGF receptors (Owen, A. et al. (1984) Science 225:54-56). Similar properties were shown for the sis/PDGF-2 gene product derived from cultured normal human cells (for example, human arterial endothelial cells), or from human malignant cells expressing the sis/PDGF-2 gene (Antoniades, H. et al. (1985) Cancer Cells 3:145-151).

The recombinant PDGF-2 homodimer (referred to as recombinant PDGF herein) is obtained by the introduction of cDNA clones of c-sis/PDGF-2 gene into mouse cells using an expression vector. The c-sis/PDGF-2 clone used for the expression was obtained from normal human cultured endothelial cells (Collins, T., et al. (1985) Nature 216:748-750).

Wound Healing

To determine the effectiveness of PDGF/EGF mixtures in promoting wound healing, the following experiments were performed.

Young white Yorkshire pigs (Parson's Farm, Hadley, Mass.) weighing between 10 and 15 kg were fasted for at least 6 hours prior to surgery and then anesthetized. Under aseptic conditions, the back and thoracic areas were clipped, shaved, and washed with mild soap and water. The area to be wounded was then disinfected with 70% alcohol.

Wounds measuring 1 cm×2 cm were induced at a depth of 0.5 mm using a modified Castroviejo electrokeratome (Storz, St. Louis, Mo., as modified by Brownells, Inc.). The wounds resulted in complete removal of the epithelium, as well as a portion of the underlying dermis (comparable to a second degree burn injury). Individual wounds were separated by at least 15 mm of unwounded skin. Wounds receiving identical treatment were organized as a group and separated from other groups by at least 3 cm. Wounds receiving no growth factor treatment were separated from wounds receiving such treatment by at least 10 cm.

The wounds were treated directly with a single application of the following growth factors suspended in biocompatible gel: 1) 500 ng pure human PDGF (purified by high performance liquid chromatography) or recombinant PDGF alone; (2) 500 ng pure recombinant PDGF in combination with up to 5000 ng human, mouse, or recombinant EGF, (3) 500 ng human, mouse, or recombinant to 5000 ng recombinant human EGF alone.

Following wounding, biopsy specimens were taken on days 3 through 10. Biopsy specimens for histologic evaluation were taken as wedges approximately 3 mm deep and placed in 10% formalin. Specimens for biochemical analysis and autoradiography were obtained using an electrokeratome. The final dimensions of the specimens were 1.5 mm×10 mm×1.5 mm. Three specimens per wound were collected for biochemical analysis. Following collection, the specimens were frozen in liquid nitrogen and stored at −80° C. The biopsy specimens were analyzed as follows.

Histologic Evaluation

Histologic specimens were prepared using standard paraffin impregnating and embedding techniques. Four micron sections were made and stained using filtered Harris hemotoxylin and alcoholic eosin; they were then observed under a microscope. All specimens were scored blindly by two investigators at equally distributed points throughout the sections. The widths of the epithelial and connective tissue layers were scored using a grid placed within the ocular of the microscope; the measurement was then converted into millimeters using a micrometer viewed under the same conditions. Cell density was determined by counting the number of nuclei per grid area.

Collagen and Protein Determination

Hydroxy-proline content (i.e., collagen) was determined in the 1.5 mm wide frozen cross-sections by separating the newly formed wound tissue from the remaining tissue under a dissecting microscope. The wound tissue was hydrolized in 6M HCl overnight at 120° C. and hydroxyproline analyses were performed on the hydrolysate as described previously (Switzer et al., Anal. Biochem. 39, 487 (1971).

Protein content of the tissue extract in concentrated ammonium hydroxide was measured by the Bradford method (Bradford (1976) Anal. Biochem. 72:248–54), with bovine serum albumin as a standard. Results The results from histologic evaluation indicated that wounds treated with the combination of recombinant EGF and PDGF in a weight to weight ratio of 5:1 to 10:1 had thicker connective tissue with more collagen (about 2.0 fold increase over controls) and epithelial layers (about 0.8 fold increase over controls), and more extensive epithelial projections connecting these layers, than wounds receiving no treatment, human or recombinant EGF alone, or pure PDGF alone. The PDGF/EGF treated wounds also had greater cellularity, protein and collagen contents.

Dosage

To determine the appropriate dosage of purified PDGF and EGF, the above-described experiments were repeated except that the wounds were treated with 5 ng, 10 ng, 20 ng, and 30 ng purified PDGF and EGF per square millimeter of wound dispersed in 30 $\mu l$ of biocompatible gel. The results showed that optimum effects were produced when the PDGF content was 4 $ng/mm^2$ or higher and EGF was 20 $ng/mm^2$ or higher.

To determine the appropriate ratio of pure PDGF to EGF, combinations in which the weight to weight ratio of PDGF to EGF ranged from 1:10 to 25:1 were evaluated as described above. Optimum results were achieved with ratios greater than 1:5.

Other embodiments are within the following claims.

1. A method for healing an external wound of a mammal comprising applying to said wound a wound-healing amount of a composition consisting essentially of purified epidermal growth factor (EGF) and purified platelet-derived growth factor (PDGF) wherein said EGF and said PDGF are present in a weight to weight ratio of at least 5:1, respectively.

2. The method of claim 1 wherein the weight to weight ratio of said EGF to said PDGF in said composition is at lest 10:1.

3. A method of healing an external wound of a mammal comprising applying to said wound a wound-healing amount of a composition consisting essentially of purified PDGF and purified EGF in a weight-to-weight ratio of at least 5:1, wherein said EGF is present in said composition at a concentration of at least 500 ng/150 $mm^2$ in said wound.

4. The method of claim 3, said EGF being present at a concentration of at least 5000 ng/150 $mm^2$ in said wound.

* * * * *